United States Patent [19]

Holtzman et al.

[11] Patent Number: 5,558,626
[45] Date of Patent: Sep. 24, 1996

[54] AMBULATORY ARM ELEVATION SLING

[76] Inventors: Elizabeth Holtzman, 180 Bergen St., Brooklyn, N.Y. 11217; Lynn Bassini, 479 10th St., Brooklyn, N.Y. 11215; Mukund R. Patel, 35 Annfield Ct., Staten Island, N.Y. 10304

[21] Appl. No.: 200,156

[22] Filed: Feb. 23, 1994

Related U.S. Application Data

[63] Continuation-in-part of Ser. No. 942,142, Sep. 8, 1992, abandoned.

[51] Int. Cl.$^6$ ............................... A61F 5/00; A61F 5/37
[52] U.S. Cl. ............................ 602/4; 128/869; 128/878
[58] Field of Search ..................... 128/846, 869, 128/870, 874–879, 881, 882; 602/4, 5, 20, 21

[56] References Cited

U.S. PATENT DOCUMENTS

| | | |
|---|---|---|
| 826,648 | 7/1906 | Challenger ................... 128/878 X |
| 1,257,297 | 2/1918 | Brown . |
| 1,639,815 | 6/1924 | Siebrandt . |
| 1,976,244 | 6/1932 | Moran . |
| 2,180,270 | 11/1939 | Anderson et al. ............. 128/878 X |
| 2,358,551 | 6/1943 | Beaton . |
| 2,484,130 | 4/1947 | Thibault . |
| 2,703,082 | 3/1955 | Emert ........................ 128/881 |
| 3,188,090 | 6/1965 | Job ......................... 128/878 X |
| 3,515,131 | 10/1968 | Stevens . |
| 3,554,194 | 1/1971 | Johnson . |
| 3,706,310 | 12/1972 | Garnett . |
| 3,815,588 | 6/1974 | Klausner . |
| 4,048,991 | 9/1977 | Marx . |
| 4,091,808 | 5/1978 | Nelson ...................... 178/882 |
| 4,214,579 | 7/1980 | Ford . |
| 4,417,570 | 11/1983 | Finneston . |
| 4,437,459 | 3/1984 | Slavetskas . |
| 4,572,172 | 2/1986 | Williams . |
| 4,598,702 | 7/1986 | Lilla ........................ 602/4 |
| 4,610,244 | 9/1986 | Hammond .................... 128/876 |
| 4,613,179 | 9/1986 | van Zelm . |
| 4,620,535 | 11/1986 | Nesbitt . |
| 4,625,719 | 12/1986 | Chambers ..................... 602/4 |
| 4,644,940 | 2/1987 | Nakamura . |
| 4,751,923 | 6/1988 | Marim ..................... 128/878 X |
| 4,759,353 | 7/1988 | Melendez et al. . |
| 4,895,142 | 1/1990 | Liptak .................... 128/878 X |
| 4,905,713 | 3/1990 | Morante . |
| 5,016,650 | 5/1991 | Marlar ....................... 128/878 |
| 5,031,639 | 7/1991 | Wolfer ....................... 128/874 |
| 5,033,461 | 7/1991 | Young et al. . |
| 5,060,638 | 10/1991 | Bodine, Jr. ................ 128/878 X |
| 5,065,732 | 11/1991 | Smith ........................ 124/80 |
| 5,076,288 | 12/1991 | Millard et al. ............. 128/878 X |
| 5,120,300 | 6/1992 | Shaw ...................... 128/876 X |
| 5,188,587 | 2/1993 | McGuire et al. ............... 602/70 |
| 5,329,941 | 7/1994 | Bodine, Jr. .................. 128/878 |
| 5,358,470 | 10/1994 | Johnson .................... 602/4 X |
| 5,393,300 | 2/1995 | Bauerfeind et al. .......... 128/876 X |

FOREIGN PATENT DOCUMENTS

| | | | |
|---|---|---|---|
| 2648704 | 12/1990 | France . | |
| 219219 | 2/1910 | Germany ................... 128/878 |
| 4137381 | 5/1993 | Germany ................... 128/881 |
| 8203596 | 4/1983 | Netherlands ............... 128/878 |
| 112684 | 1/1918 | United Kingdom . | |
| 1150072 | 4/1969 | United Kingdom . | |

*Primary Examiner*—Robert A. Hafer
*Assistant Examiner*—Brian E. Hanlon
*Attorney, Agent, or Firm*—Curtis Morris & Safford P.C.

[57] ABSTRACT

An improved sling for maintaining a patient's hand in an elevated position while permitting substantially unrestrained mobility of the patient's shoulder consists essentially of an arm strap wrappable about the patient's upper arm and lower arm to form a loop with overlapping end portions having surfaces which face each other. These overlapping, facing surfaces are provided with removable adhesive material, such as hook-and-loop material so as to form (when the elbow is bent) an arm loop of adjustable length to establish the bend of the patient's elbow and elevation of the patient's hand. A palm band (or hand loop) for receiving and locating the patient's hand in predetermined position is fixed to one end portion of the arm strap, the latter having a length and width matched to the size of the patient's arm.

21 Claims, 5 Drawing Sheets

AMBULATORY ARM ELEVATION SLING

This is a continuation-in-part of application Ser. No. 07/942,142, filed Sep. 8, 1992 now abandoned.

BACKGROUND OF THE INVENTION

This invention relates to a sling and, more particularly, to an ambulatory arm elevation sling which elevates a patient's hand while permitting substantially unrestrained mobility of the patient's shoulder.

Several types and configurations of arm slings have been proposed over the years; but perhaps the most common sling presently in use is formed simply of fabric tied about a patient's neck in triangular configuration with the base of the triangle supporting and locating the patient's forearm. The altitude of the triangle defines the elevation of the arm. While this sling is generally inexpensive to manufacture, it suffers from notable disadvantages. For example, since the intent of this sling is to immobilize the patient's affected arm, the patient is permitted free use of only one hand, namely, the opposite hand; and adjustments to the sling with only one hand are generally difficult, if not impossible. That is, adjustments to the elevation provided by the sling while that sling is in use are quite difficult.

Another disadvantage associated with this type of simple prior art sling is that the patient's arm generally is rendered immobile and non-functional. While this immobility is desired in many instances, such as in the event of an injury to the patient's shoulder or other trauma which would be further aggravated but for such immobility, the restraint occasioned by the sling is to be avoided when the nature of the injury does not mandate immobilization. For example, the use of a sling often is prescribed to aid in the reduction of edema or the healing of an elbow or hand injury, the nature of which does not necessitate immobilization of the patient's shoulder. While the typical prior art sling may be adapted to maintain the patient's hand in a limited elevated position, such as at a height above the patient's heart, that sling also inhibits any movement of the patient's arm. As a result, prolonged use of the sling may result in a stiff elbow and a "frozen shoulder."

Recognizing the difficulty of providing a universal sling to treat all injuries, trauma and recuperation to arms, hands and elbows, the prior art has developed slings for specialized purposes. For example, U. K. Patent No. 112,684 describes an appliance to maintain a patient's hand in a predetermined, upraised bent position. This appliance is relatively difficult to manufacture and, thus, is expensive; and it also is difficult for the patient to adjust. Furthermore, this appliance by itself is not sufficient to elevate the patient's hand and must be used with other slings, such as the aforementioned triangular sling, to do so.

U.S. Pat. No. 3,554,194 suggests an alternative to the simple triangular sling and is formed of a relatively narrow strap, or belt, having a buckle to define a figure "8" in which one loop thereof is positioned about the patient's neck and the other loop supports the patient wrist. While adjustments to this sling may be made with one hand relatively simply, two hands clearly are needed to thread the buckle. Furthermore, since this sling must be worn about the patient's neck, it inherently limits mobility of the shoulder. Still further, this sling provides limited elevation of the arm by shortening the effective length of the strap about the patient's neck; but as more elevation is needed, the strap is shortened further, resulting in excessive pressure exerted on the neck. Consequently, this sling is uncomfortable to wear and rarely is adjusted to provide ideal elevation, for example, elevation above the heart.

In addition, some hand or wrist injuries are best treated by general immobilization of the patient's arm, at least temporarily or for certain periods of time. It may be preferred to immobilize the arm at some times and permit shoulder movement at other times. Various appliances are known to render a patient's arm immobile, but they are complicated, difficult to use and often cannot be manipulated solely by the patient. Hence, a relatively simple device that can be used with a sling so as to immobilize the patient's arm if immobilization is prescribed and that can be handled by a patient without outside assistance is desired.

OBJECTS OF THE INVENTION

Therefore, it is an object of the present invention to provide an improved sling which overcomes the aforementioned disadvantages and drawbacks associated with the prior art.

Another object of this invention is to provide a sling of relatively simple and inexpensive construction which, when used, provides proper elevation of a patient's arm and positioning of the patient's hand, and does not restrict shoulder movement.

A further object of this invention is to provide a sling which is simple to put on and which permits simple one-handed adjustment when in use, thereby facilitating a change in elevation of the patient's arm.

An additional object of this invention is to provide a sling to elevate and position a patient's hand above the heart and thereby reduce edema.

Still another object of this invention is to provide an improved sling which is relatively comfortable to wear, prevents "frozen shoulder," prevents a stiff elbow and obviates the concentration of pressure at any particular location of the patient's arm or hand.

It is yet an additional object of this invention to provide an inexpensive sling that is easily adjustable for different arm lengths and that can assume different angles for the user's elbow for comfort, while nevertheless allowing limited functions of the user's hand.

Yet a further object of this invention is to provide a relatively simple sling of the aforementioned type which permits flexing of the elbow.

Another object of this invention is to provide a simple device that is easy to wear which, when used with the sling of the present invention, serves to immobilize the patient's arm, if immobilization is prescribed, thereby making the sling universally useful.

Various other objects, advantages and features of the present invention will become readily apparent from the ensuing detailed description, and the novel features will be particularly pointed out in the appended claims.

SUMMARY OF THE INVENTION

In accordance with this invention, an improved sling is provided for maintaining a patient's upper extremity, i.e. the patient's hand, wrist or lower arm, in an elevated position while permitting substantially unrestrained mobility of the patient's shoulder. The sling consists essentially of an arm strap wrappable about the patient's upper arm and lower arm (when the elbow is bent) to form a loop with overlapping end portions having surfaces which face each other. The overlapping end portions are provided with removably sewing material, such as hook-and-loop material, so as to form an arm loop of adjustable length to establish the angle of the patient's arm at the elbow and establish desired elevation of the patient's hand. If desired, the entire length of the arm strap may be provided with such removably securing material. A palm band (or hand loop) for receiving and locating the patient's hand in predetermined position is fixed to one end portion of the arm strap, the latter having a length and width appropriate to the size of the patient's arm. Preferably, the arm strap is comprised of foam material for the comfort of the patient. Similarly, in the preferred embodiment, the palm band also is comprised of foam material.

In one embodiment, the palm band may be formed as a loop of adjustable size, for example, it may be constructed of hook-and-loop material to permit size adjustment to match the patient's hand.

The sling of the present invention is adaptable for universal use and may be utilized by a patient to immobilize the patient's arm if immobilization is prescribed. Immobilization is achieved by wrapping a waist band or belt about the patient, the waist band having an outer surface to which a facing surface of the arm strap is removably adhereable. For example, the outer surface of the waist band may be provided with hook-type material and the facing surface of the arm strap may be provided with loop-type material, whereby the arm strap adheres to the waist band to immobilize the patient's shoulder. Hence, temporary immobilization may be achieved to allow periods of rest and further elevation. The patient may easily detach the arm strap from the waist band simply by raising the patient's arm.

BRIEF DESCRIPTION OF THE DRAWINGS

The following detailed description, given by way of example and not intended to limit the present invention solely thereto, will best be understood in conjunction with the accompanying drawings in which.

DETAILED DESCRIPTION

Referring now to FIGS. 1–5, wherein like reference numerals are used throughout, a sling 100 exhibiting the desirable features and advantages of the present invention is illustrated.

Figure 4:
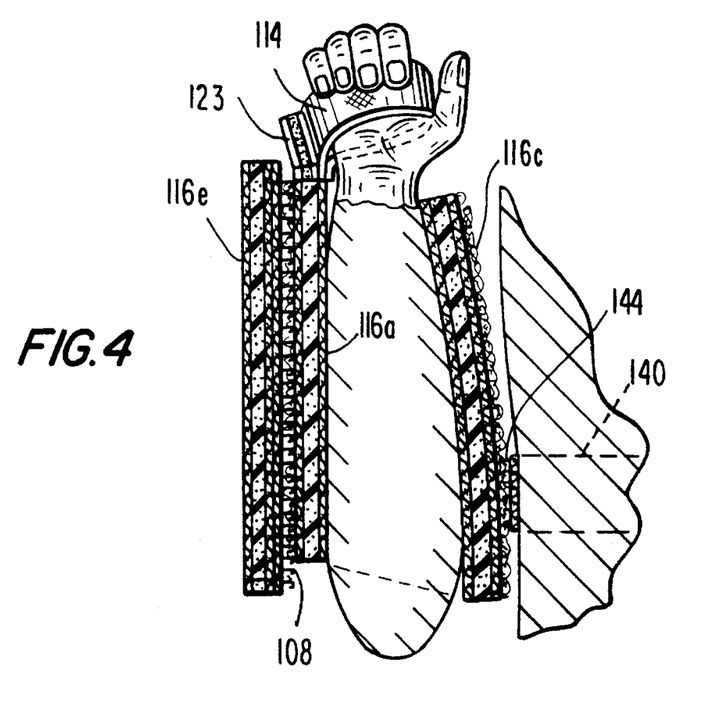
FIG. 4 is a view taken along lines 4—4 in FIG. 3.
Figure 5:
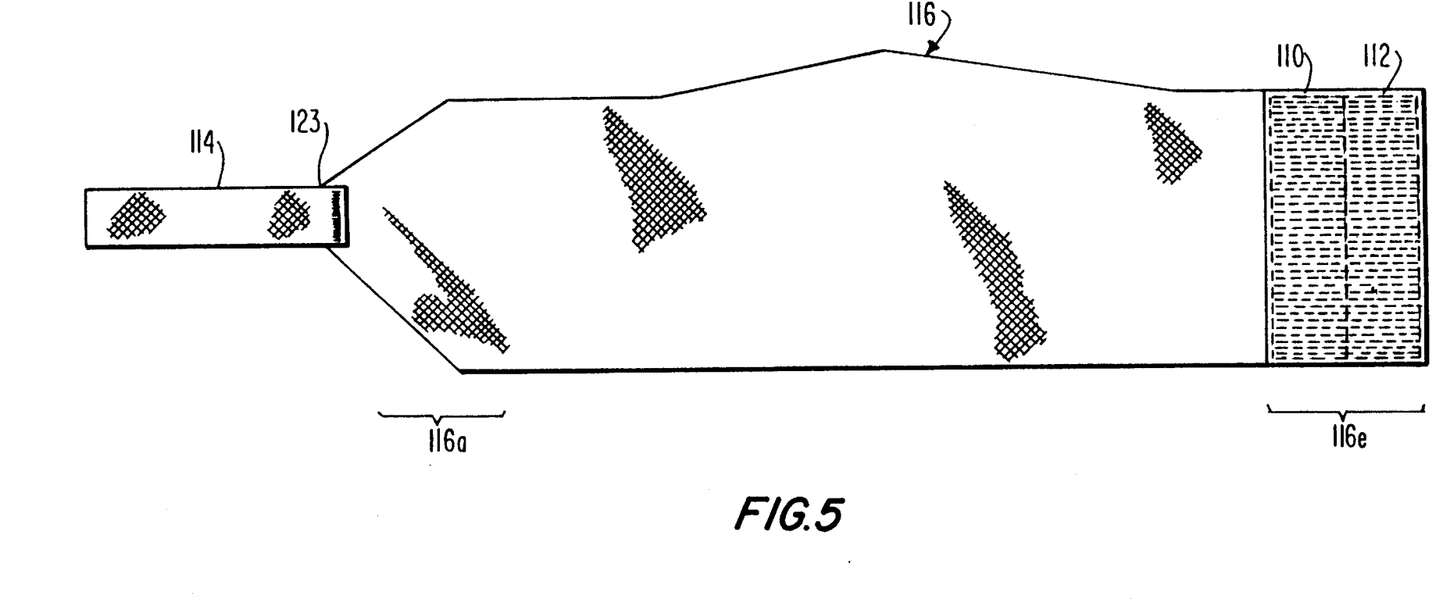
FIG. 5 is an elevational view of the sling when not in use.

FIGS. 1–4 represent the manner in which the sling is used by a patient and FIG. 5 is an elevational view of the sling which, as is apparent, is adapted to be wrapped around the patient's arm, thereby elevating the patient's hand to a desired location, preferably above the heart so as to reduce edema. The sling is comprised of an arm strap 116 which is generally rectangular in shape, such as shown in FIG. 5, having a length and width that are appropriate to the size of the patient's arm and size of the patient's body (for example, a small patient may have a large or fat arm and a large patient may have a thin arm). For example, the length of the arm strap may be in the range of 12 to 36 inches and the width thereof may be in the range of 4 to 15 inches. A desirable, but not necessarily limiting, numerical example is a length on the order of about 24 inches and a width on the order of about 8 to 8½ inches.

Arm strap 116 is formed of fabric material, such as woven cotton, synthetic material or other material used heretofore in like applications. In one preferred construction, the arm strap is formed of foam material sandwiched between layers 104 and 106 (best seen in FIG. 2), these layers having outwardly facing surfaces comprised of loop-type material 102 which, as will be described, are particularly adapted to be removably adhereable to hook-type material, the resultant hook-and-loop material being of the type sold under the trademark "VELCRO". As is apparent from FIGS. 1–4, arm strap 116 is adapted to be wrapped about the patient's arm and, in particular, when the patient's elbow is bent, the arm strap is wrappable about the patient's upper arm and lower arm so as to maintain the elbow in its bent configuration. As a result of this wrapping of the arm strap about the patient's arm, shown most clearly in FIGS. 1–3, opposite end portions 116a and 116e of the arm strap overlap each other. A strip 112 of hook-type material is disposed across the width of arm strap 116 at one end thereof, such as end 116e shown in FIG. 5, and in a preferred embodiment, two such strips 110 and 112 are so provided. These strips of hook-type material are seen to adhere to the loop-type material provided on the surface of the arm strap which faces strips 110, 112, shown more particularly in FIGS. 1 and 2. Consequently, end 116e of arm strap 116 upon which strips 110, 112 are provided removably adheres to the opposite end 116a of the arm strap. Alternatively, strips 110 and 112 may be replaced simply by providing hook-like material 108 directly on the surface of end portion 116e which faces end portion 116a when arm strap 116 is wrapped about the patient's arm.

A palm band 114, which also may be formed at least in part of foam material, is secured to end 116a of arm strap 116 at juncture 123 by, for example, stitching or any other suitable fixing means. Alternatively, the palm band may be formed integrally with end 116a. As shown more clearly in FIGS. 1, 3 and 4, palm band 114 is adapted to receive and, thus is wrapped about the palm of the patient's hand, thereby initially positioning sling 100. Thereafter the patient may, with the patient's other hand, grasp end 116e and wrap this end about the upper arm, under the patient's axilla, about the patient's lower arm and then into contact with end 116a, thus forming the loop shown in FIGS. 1–4. It is appreciated that the size of this loop is adjustable simply by positioning end 116e along any desired location of end 116a. The size of the loop is dependent, in part, upon the size of the patient's arm and, more importantly, the size of the loop determines the amount of elevation of the patient's hand. It will be appreciated that a smaller loop tends to elevate the patient's hand higher because it brings the patient's lower arm closer to the upper arm. Conversely, a larger loop tends to reduce the elevation of the hand.

In a preferred embodiment, palm band 114 exhibits a loop whose half-length (i.e., when the loop formed of the palm band is collapsed or flat) is on the order of 3 to 7 inches and, in one non-limiting numerical example, is on the order of about 5 inches. This accommodates the patient's hand comfortably.

Although not shown, palm band 114 may be adjustable in size as, for example, by forming the palm band as a length of material having one end secured to juncture 123 and an opposite free end. The free end of the palm band, that is, the end thereof which is remote from juncture 123, is brought back to form a loop. The size of this loop is determined by the location at which the free end of the palm band contacts the length thereof; and removably adhesive material, such as hook-and-loop material, may be provided on the contacting portions of the palm band. That is, rather than forming a palm band of fixed loop, the loop may be adjustable so as to accommodate hands of different sizes.

When in use, arm strap 116, as deployed about the patient's arm, may be thought of as having discrete sections even though the overall length of the arm strap is continuous. As shown more particularly in FIGS. 1 and 2, end 116a, to which palm band 114 is secured, extends from the patient's forearm to the patient's upper arm, section 116b is deployed about rear of the patient's upper arm, section 116c extends from the patient's upper arm to the patient's forearm and is disposed closest to the patient's chest, section 116d is deployed about the patient's forearm and extends to end portion 116e. Preferably, the arm strap is sufficiently wide to distribute pressure inherently exerted by the arm strap on the radial nerve in the upper arm of the patient. For comfort, the arm strap is constructed of foam or similar material, as mentioned above. Alternatively, portion 116b of arm strap 116 may be provided with a pressure pad slidable thereon to a location so as to accommodate that portion of the upper arm of the patient which alleviates pressure otherwise applied to the radial nerve.

In the preferred embodiment, and for ease and simplicity of manufacture, substantially the entire outer surface of layer 106 may be provided with loop-type material, thereby accommodating the positioning of hook-type material 108 on the facing surface of end portion 116e regardless of the size of the loop formed by the arm strap. Alternatively, however, only that portion of the outer surface of layer 106 disposed in the vicinity of end portion 116a need be provided with such loop-type material because, in the expected use of sling 116, only end portions 116a and 116e are expected to overlap with and thus face each other.

Layer 104 of arm strap 116 preferably may be formed of material which provides proper comfort to the patient, particularly since it is expected that layer 104 may, in many applications, be in direct contact with the patient's skin.

As clearly shown in FIG. 5, palm band 114 is secured to end portion 116a of arm strap 116 by stitching to define juncture or joint 123. Alternatively, other fastening means are contemplated to secure the palm band to the arm strap, such as snaps, rivets, adhesive, or the like. As yet another alternative, the palm band and arm strap may be of one-piece construction.

When the sling is used by the patient, the inner surface of palm band 114 is in contact with the patient's palm and, desirably, exerts dorsal flexion on the hand so as to locate it in a predetermined, upwardly bent position. As mentioned above, palm band 114 preferably is formed of foam or similar material to facilitate comfort and avoid concentration of pressure at any location on the patient's hand. Although the entirety of the palm band may be formed of such foam material, if desired, only that portion thereof which is in contact with the patient's palm, shown in FIGS. 1 and 4 as the inner surface of the palm band, may be provided with a strip of foam material. Additionally, to impart sufficient dorsal flexion to the patient's hand, portions of palm band 114 optionally may be provided with elastic material. For example, a portion of the palm band at or in the vicinity of juncture 123 may be formed of elastic material, although it should be readily appreciated that other or additional portions of the palm band may be formed of such material.

It will be seen that sling 100, when applied as shown in FIGS. 1–4, does not substantially limit the rotation of the patient's shoulder. Hence, the possibility of "frozen shoulder" is minimized. Furthermore, the ease in adjusting the elevation of the patient's arm, particularly by way of adjustments which may be made with the patient's free hand, prevents numbness that otherwise might be present if the elbow is bent too tightly.

Figure 1:
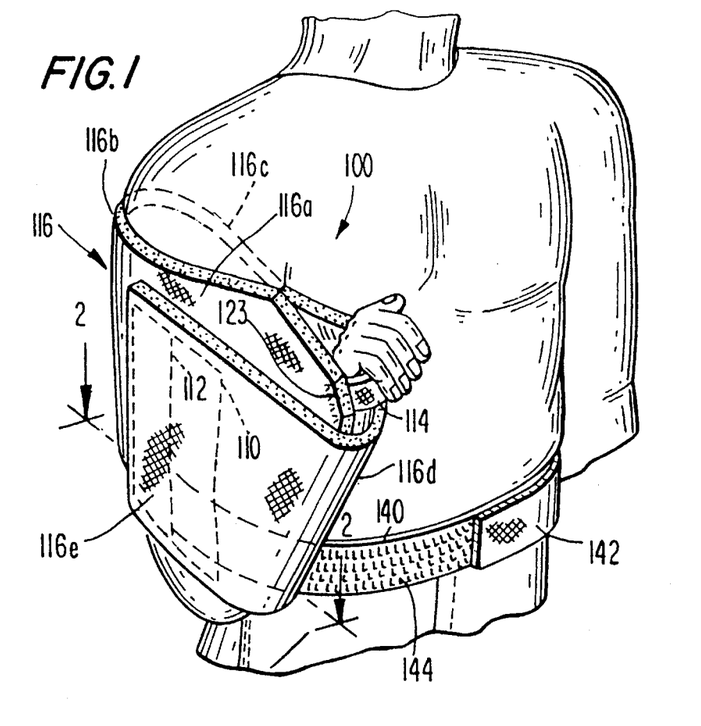
FIG. 1 is a perspective view of a preferred embodiment of the sling in accordance with the present invention.
Figure 2:
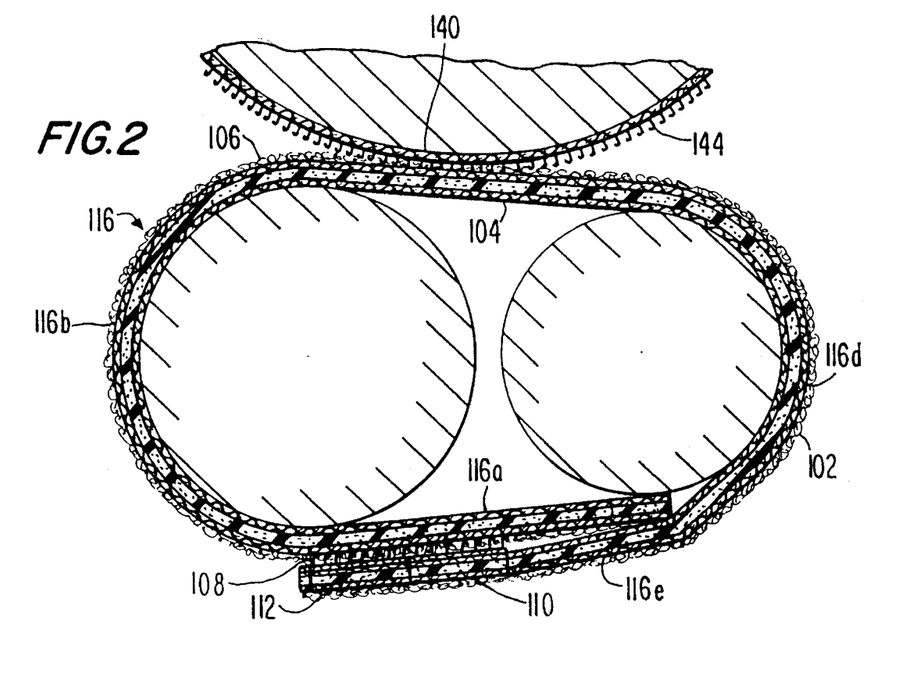
FIG. 2 is a sectional view taken along lines 2—2 of FIG. 1.
Figure 3:
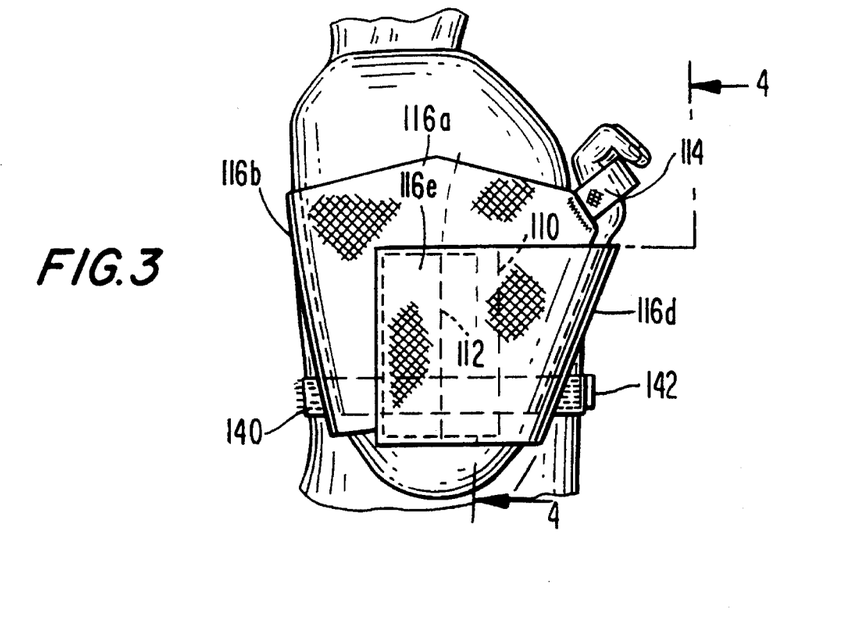
FIG. 3 is a side view of the elevation sling of the present invention when used by a patient.

In addition to permitting unrestrained mobility of the patient's shoulder, sling 100 also may be used, when so prescribed, in combination with a waist band or belt 140 (FIGS. 1–4) adapted to removably adhere the sling thereto in a manner so as to maintain the patient's arm in close proximity to the patient's body, thereby immobilizing the arm to ensure that the hand is properly elevated. Waist band 140, when worn about the patient's waist, may be provided with an outer surface having hook-type material 144 thereon. If the inner surface of the waist band is provided with loop-type material, it is appreciated that the hook-type material on the outer surface of the waist band adheres to the loop-type material on the inner surface thereof when an end 142 is brought into contact with the band. Such hook-and-loop material thus permits the size of the waist band to be adjusted. Additionally, hook-type material 144 disposed on the outer surface of waist band 140 is adapted to contact the loop-type material provided on the outer surface of layer 106 of arm strap 116 of sling 100, preferably at section 116c, such as shown in FIGS. 2 and 4, thereby removably securing the sling to the waist band. As a result of the facing hook-and-loop material provided on waist band 140 and arm strap 116, the arm strap adheres to the waist band to immobilize the patient's arm and ensure proper elevation of the hand. Of course, the sling may be easily and quickly detached from the waist band as may be needed.

Consequently, sling 100 exhibits universal utility inasmuch as, when used without waist band 140, it permits unrestrained mobility of the patient's shoulder; and when used with the waist band, the sling disposes the patient's arm and hand in proper elevation while immobilizing the patient's shoulder.

Figure 6:
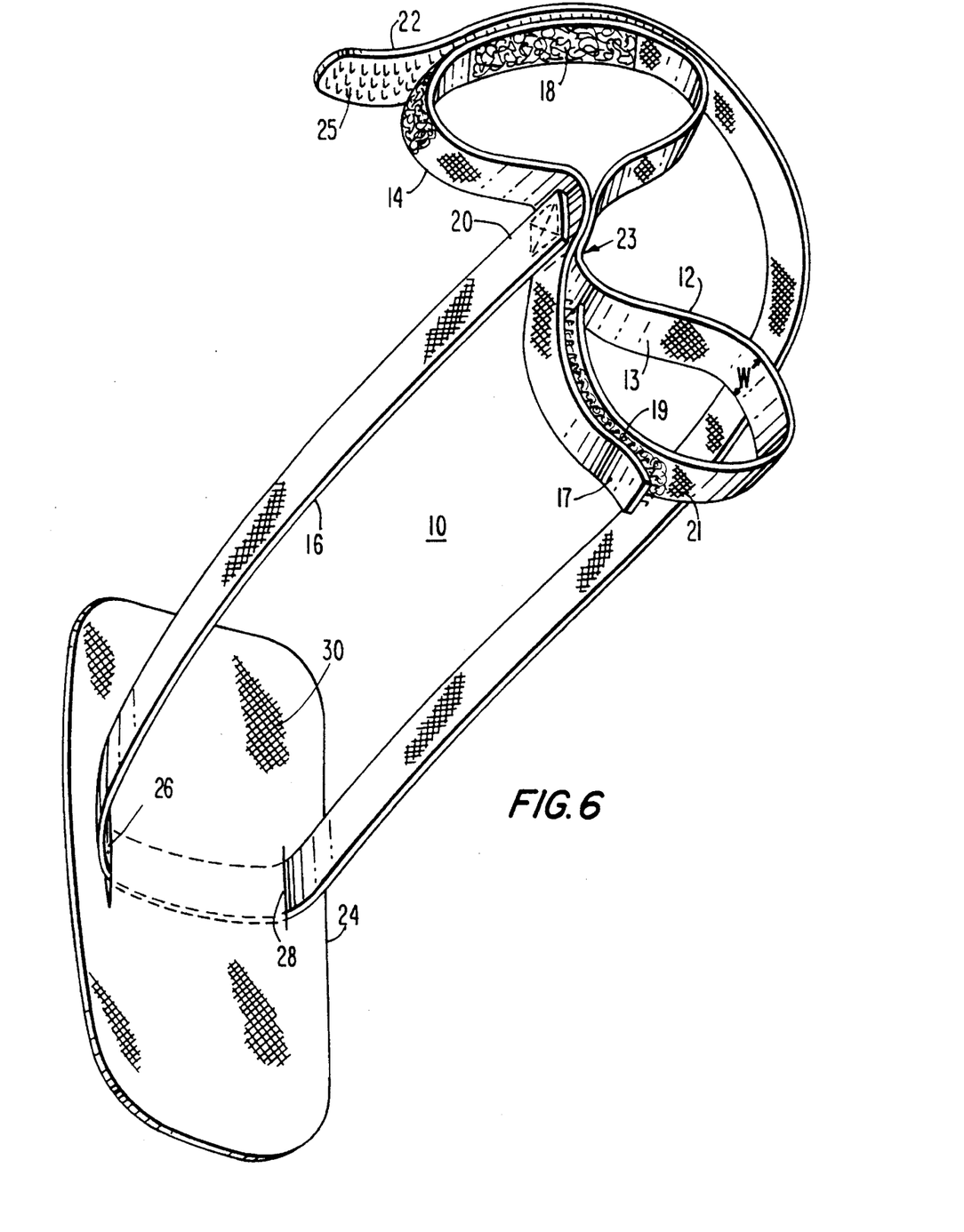
FIG. 6 is a perspective view of another version of an arm elevation sling.
Figure 7:
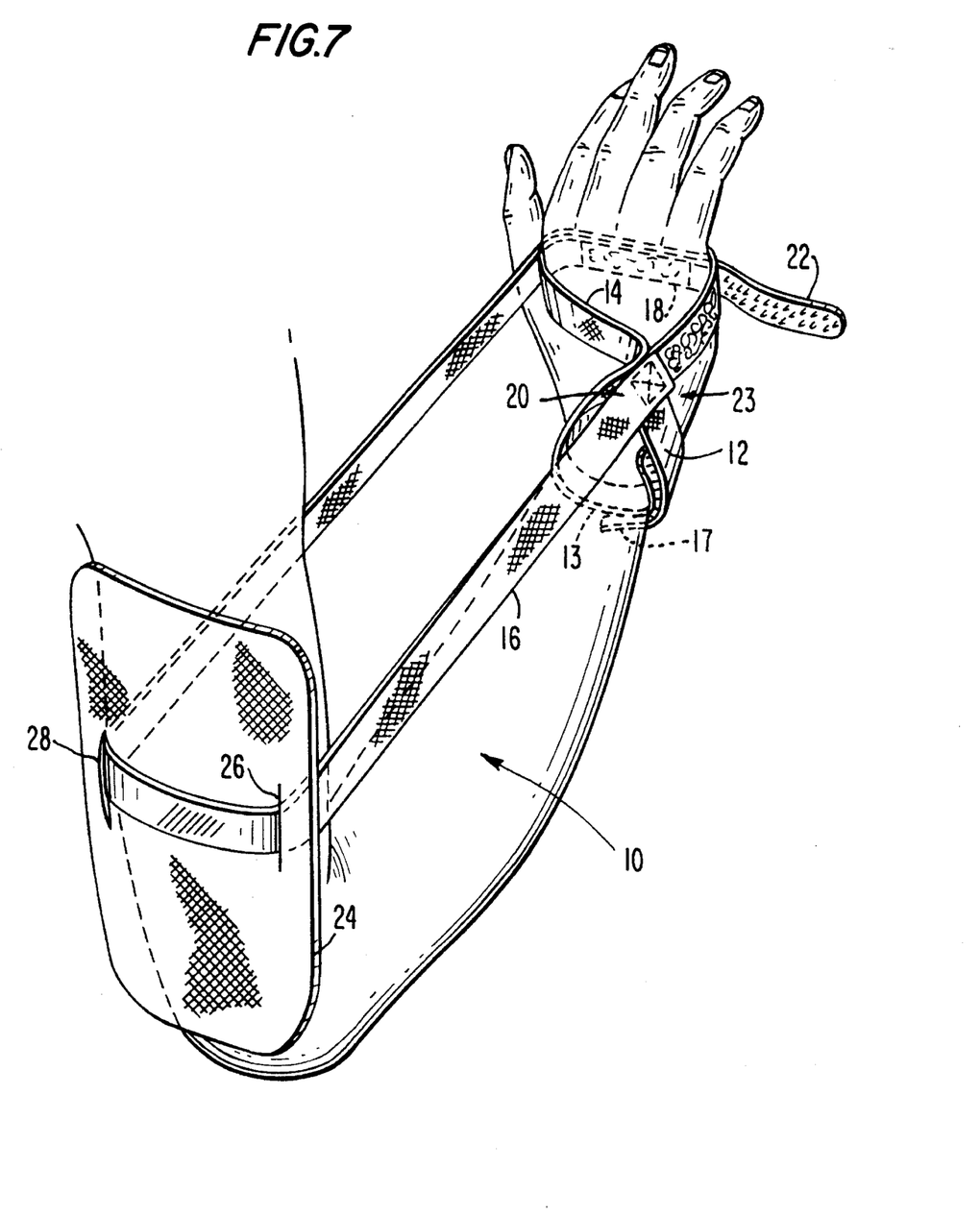
FIG. 7 is a schematic representation of the manner in which the sling of FIG. 6 is used to elevate and position a patient's hand.

FIG. 6 illustrates a sling 10 exhibiting many of the desirable features and advantages of the sling shown in FIGS. 1–5. As illustrated, sling 10 is comprised of a wrist band 12, a palm band 14 and an upper arm strap 16. Wrist band 12 is formed of fabric material, such as the aforementioned woven cotton, synthetic material or other material used heretofore in like applications. Preferably, the width W of the wrist band need be no greater than that which is sufficient to support the patient's wrist with or without a cast thereon. For example, width W may be in the range of one-half inch to about 2 inches. As is apparent, wrist band 12 includes an inner surface 13 which, as shown in FIG. 7, is in contact with the patient's wrist. As also shown, the diameter of the wrist band preferably is large enough to permit the patient's hand to pass easily therethrough and fit loosely around the wrist for supporting same.

Desirably, to accommodate wrists of different sizes or to accommodate a cast that may be placed over the patient's wrist, wrist band 12 is made adjustable. In the illustrated embodiment, the wrist band has a free end 17 that is provided with removably adhesive material such as hook-and-loop material, to adhere to a facing portion of the wrist band. For example, hook material 19 is provided on a segment of free end 17 and the remainder of the outer surface of wrist band 12 is provided with loop material 21. To tighten the wrist band as needed, the patient merely pulls free end 17 and then contacts hook material 19 with loop material 21 to fix the size of the wrist band.

Palm band 14 may be similar to aforementioned palm band 114 and may be comprised of a fabric similar to that of wrist band 12 and, in one embodiment, is formed as a loop adapted to be secured at one tangential portion thereof to the wrist band, as illustrated at joint 23. Preferably, the palm band is secured to the wrist band at 23 by sewing or stitching, but other fastening means are contemplated, such as snaps, rivets, adhesive, or the like. Joint 23 generally need not be subjected to large rotational movements and, therefore, there is no overall requirement for the fastening means used at this joint to be pivotable. If desired, palm band 14 may be adjustable in a manner similar to that shown for wrist band 12.

As shown in FIG. 7, when sling 10 is in use, the inner surface of palm band 14 is in contact with the patient's palm and, desirably, exerts dorsal flexion on the hand so as to locate it in a predetermined, upwardly bent position. To facilitate comfort and avoid concentration of pressure at any location of the patient's hand, the inner surface of palm band 14 may be provided with a strip 18 of foam or similar material of conventional type normally used in similar applications. Strip 18 may be of limited length; but it is appreciated that there need be no limitation on the actual length of this strip. If desired, strip 18 may be substantially coextensive with the length of palm band 14.

Portions of palm band 14 may be provided with elastic material to exert dorsal flexion on the patient's hand. For example, a portion of predetermined length at or in the vicinity of joint 23 whereat the palm band is secured to wrist band 12 may be formed of elastic material; and other or additional portions of the palm band may be formed of such material. For example, the fabric from which palm band 14 is made may exhibit suitable elasticity; and it is further appreciated that strip 18 of foam material, if secured to such elastic material, likewise should exhibit sufficient elasticity such that the strip does not separate from the palm band.

Arm strap 16 is formed of a web of fabric material and is fixed at one end 20 to wrist band 12 at or in the vicinity of joint 23. End 20 of arm strap 16 simply is sewn to the wrist band at joint 23 and the other end 22 of the arm strap is releasably fixable to palm band 14, and is further described below.

As shown in FIG. 7, when end 22 of arm strap 16 is fixed to palm band 14, a large loop about the patient's upper arm is formed. The size of this loop is, of course, dependent upon the length of arm strap 16 from joint 23 at end 20 to the location at opposite end 22 whereat the arm strap is fixed to palm band 14. This loop defines the degree of bend in the patient's arm when sling 10 is used by the patient. As a result, the elevation of the patient's hand likewise is established; and this elevation may be increased by decreasing the size of the loop and, conversely, the elevation may be reduced by increasing the loop size. A greater bend in the patient's elbow results in greater elevation of the hand; and this is facilitated by reducing the size of the loop, as by selecting the location along end 22 at which the arm strap is secured to palm band 14.

To distribute the pressure inherently exerted by arm strap 16 on the radial nerve in the upper arm of the patient, a pressure pad 24 is slidably secured to the arm strap. In the illustrated embodiment, this pressure pad is of generally rectangular shape, although the particular shape thereof is of little importance and other suitable shapes, such as ellipsoid, circular, or the like, may be selected. Slits 26 and 28 are provided in pressure pad 24 to receive arm strap 16. These slits permit the pressure pad to slide along the length of the arm strap to any desired location and, thus, sling 10 may be adapted to accommodate arms of various lengths and widths. Hence, sling 10 is usable by virtually any patient. Although not necessary, to facilitate comfort, the inner surface of pressure pad 24, that is, the surface of the pressure pad which, when in use, contacts the patient's upper arm, is provided with foam or similar material 30. This foam material may be substantially coextensive with the pressure pad. Alternatively, the foam material is of reduced area and, for example, may be centered on the pressure pad. Preferably, pressure pad 24 is formed of bendable material, such as plastic.

As yet another alternative, pressure pad 24 need not be used. Nevertheless, to improve the patient's comfort and avoid the concentration of force on the radial nerve, arm strap 16 may include a portion of larger width to carry out the pressure distribution function of pressure pad 24.

FIG. 6 best illustrates the manner in which end portion 22 of arm strap 16 is releasably secured to palm band 14. Preferably, the entire outer surface of the palm band (or at least a substantial portion of the outer surface of the palm band) and a portion of the inner surface of arm strap 16 are provided with removably adhesive means. In the preferred embodiment, such removably adhesive means is comprised of hook-and-loop material such as the type distributed under the trademark "VELCRO"; and the hook material preferably is provided on the inner surface of arm strap 16 and the loop material is provided on the outer surface of palm band 14. FIG. 6 illustrates that hook-type material 25 is provided on the inner surface of arm strap 16 along a length of end portion 22 so as not to interfere with the patient's arm. Alternatively, a relatively small area of loop-type material may be provided on the palm band and a larger length of hook-type material 25 may be provided along the inner surface of arm strap 16. Of course, the hook-type material may be provided on the outer surface of the palm band and the loop-type material may be provided on the inner surface of the arm strap, if desired. Furthermore, if it is less expensive to do so, hook-type material 25 may be provided along the entire length of arm strap 16, although the material may present some discomfort to the patient by reason of its continual contact with the patient's skin.

The adjustability of the effective length of arm strap 16 is readily apparent. After passing the hand through wrist band 12 into contact with palm band 14, the patient wraps arm strap 16 around the upper arm, such as by grasping end 22 with the other free hand, and then secures end portion 22 to palm band 14 (or, alternatively, to wrist band 12). After the patient has fixed and adjusted sling 10, further adjustments may be made if needed, or desired, simply by releasing end portion 22 of arm strap 16 from the palm band, increasing or reducing the bend of the patient's arm and then reattaching end portion 22 to the palm band.

While the present invention has been particularly shown and described with respect to particular constructions, it will be readily appreciated that various changes and modifications may be made without departing from the spirit and scope of the invention. It is intended that the appended claims be interpreted as covering the constructions that have been described herein and all equivalents thereto.

What is claimed is:

1. An improved sling for maintaining a patient's hand in an elevated position while permitting substantially unrestrained mobility of the patient's shoulder, consisting essentially of a foam fabric material arm strap wrappable around the patient's upper arm and lower arm when said patient's elbow is bent thereby forming a loop with end portions of said arm strap overlapping each other, said loop being of adjustable length to establish the bend of said patient's elbow and the elevation of said patient's hand, said arm strap having an inner surface facing the patient's arm and an outer surface and removably securing means provided on the inner and outer surfaces to maintain said arm strap in said loop wrapped around the patient's arm; and a palm band fixed to a first end of said arm strap for receiving and locating the patient's hand in predetermined position.

2. The sling of claim 1 wherein said removably securing means comprises hook-and-loop material.

3. The sling of claim 2 wherein said outer surface of said arm strap is provided with loop-type material and at least a portion of said inner surface of said arm strap is provided with hook-type material.

4. The sling of claim 3 wherein said hook-type material is provided on a strip secured to said inner surface of said arm strap.

5. The sling of claim 4 wherein said strip is secured to a second end of said arm strap, said second end being remote from said first end.

6. The sling of claim 5 wherein substantially the entire outer surface of said arm strap is provided with loop-type material.

7. The sling of claim 1 wherein said arm strap is constructed of foam material sandwiched between inner and outer layers on which are provided said removably securing means.

8. The sling of claim 1 wherein said arm strap is generally rectangular having a length and width matched to the size of the patient's arm.

9. The sling of claim 8 wherein said length is in the range of twelve to thirty-six inches and said width is in the range of four to fifteen inches.

10. The sling of claim 1 wherein said palm band is formed of foam material.

11. Improved sling apparatus for maintaining a patient's hand in an elevated position and adaptable to permit substantially unrestrained mobility of the patient's shoulder, said sling consisting essentially of a foam fabric material arm strap wrappable around the patient's upper and lower arms when said patient's elbow is bent thereby forming a loop with end portions of said arm strap overlapping each other, said loop being of adjustable length to establish the bend of said patient's elbow and the elevation of said patient's hand, said arm strap having an inner surface facing the patient's arm and an outer surface and removably securing means provided on the inner and outer surfaces to maintain said arm strap in said loop wrapped around the patient's arm, and a palm band fixed to a first end of said arm strap for receiving and locating the patient's hand in predetermined position; and a waist band wearable around the waist of said patient and having means thereon for removably securing said arm strap thereto so as to minimize mobility of said shoulder when said waist band is secured to said arm strap.

12. The apparatus of claim 11 wherein said removably securing means provided on the inner and outer surfaces of said arm strap comprises hook-and-loop material.

13. The apparatus of claim 12 wherein said outer surface of said arm strap is provided with loop-type material and at least a portion of said inner surface of said arm strap is provided with hook-type material.

14. The apparatus of claim 13 wherein said means on said waist band for removably securing said arm strap comprises hook-type material for engaging the loop-type material provided on said outer surface of said arm strap.

15. The apparatus of claim 14 wherein said hook-type material on said waistband is provided on a first surface of said waist band to contact the loop-type material on said arm strap; and said waist band includes a second surface provided with loop-type material to adhere to the hook-type material on said first surface when the waist band is wrapped around the patient's waist.

16. The apparatus of claim 14, wherein substantially the entire outer surface of said arm strap is provided with loop-type material.

17. The apparatus of claim 13 wherein said hook-type material is provided on a strip secured to said inner surface of said arm strap.

18. The apparatus of claim 17 wherein said strip is secured to a second end of said arm strap, said second end being remote from said first end.

19. The apparatus of claim 11 wherein said arm strap is constructed of foam material sandwiched between inner and outer layers on which are provided said removably securing means.

20. The apparatus of claim 11 wherein said arm strap is generally rectangular having a length and width matched to the size of the patient's arm.

21. The apparatus of claim 20 wherein said length is in the range of twelve to thirty-six inches and said width is in the range of four to fifteen inches.

* * * * *